United States Patent
Wu et al.

(10) Patent No.: US 12,227,589 B2
(45) Date of Patent: Feb. 18, 2025

(54) EPCAM ANTIBODY AND EPCAM-CAR-T CELLS

(71) Applicants: ProMab Biotechnologies, Inc., Richmond, CA (US); Forevertek Biotechnology Co., Ltd, Changsha (CN)

(72) Inventors: Lijun Wu, Berkeley, CA (US); Vita Golubovskaya, Pinole, CA (US)

(73) Assignees: Forevertek Biotechnology Co., Ltd, Changsha (CN); ProMab Biotechnologies, Inc., Richmond, CA (US)

( * ) Notice: Subject to any disclaimer, the term of this patent is extended or adjusted under 35 U.S.C. 154(b) by 708 days.

(21) Appl. No.: 17/381,537

(22) Filed: Jul. 21, 2021

(65) Prior Publication Data

US 2021/0347909 A1    Nov. 11, 2021

Related U.S. Application Data

(63) Continuation of application No. PCT/US2020/014999, filed on Jan. 24, 2020.

(60) Provisional application No. 62/796,975, filed on Jan. 25, 2019.

(51) Int. Cl.
| | |
|---|---|
| *C07K 16/30* | (2006.01) |
| *A61K 39/00* | (2006.01) |
| *C07K 14/705* | (2006.01) |
| *C07K 14/725* | (2006.01) |
| *C07K 16/28* | (2006.01) |
| *C12N 5/0783* | (2010.01) |

(52) U.S. Cl.
CPC .......... *C07K 16/30* (2013.01); *A61K 39/4611* (2023.05); *A61K 39/4631* (2023.05); *A61K 39/464466* (2023.05); *C07K 14/7051* (2013.01); *C07K 14/70521* (2013.01); *C07K 14/70578* (2013.01); *C07K 16/28* (2013.01); *C12N 5/0636* (2013.01); *A61K 2239/31* (2023.05); *A61K 2239/50* (2023.05); *C07K 2317/24* (2013.01); *C07K 2317/56* (2013.01); *C07K 2317/622* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
CPC ............. C07K 16/30; C07K 14/7051; C07K 14/70521; C07K 14/70578; C07K 2317/24; C07K 2317/622; C07K 2319/02; C07K 2319/03; C07K 2319/30; C07K 2319/33; C12N 5/0636; C12N 2510/00
See application file for complete search history.

(56) References Cited

U.S. PATENT DOCUMENTS

| | | |
|---|---|---|
| 2003/0099648 A1 | 5/2003 | Buyse et al. |
| 2016/0361360 A1 | 12/2016 | Chang et al. |
| 2017/0204177 A1 | 7/2017 | Wang et al. |
| 2018/0078640 A1 | 3/2018 | Yu et al. |

FOREIGN PATENT DOCUMENTS

| | | | |
|---|---|---|---|
| WO | 2018129248 A1 | 7/2018 | |
| WO | 2018152033 A1 | 8/2018 | |
| WO | WO-2020154627 A1 * | 7/2020 | ......... A61K 39/0011 |
| WO | WO-2024148107 A2 * | 7/2024 | |

OTHER PUBLICATIONS

International Search Report issued Apr. 27, 2020 for International Application No. PCT/US2020/014999. 4 pages.
Ang et al. "Intraperitoneal immunotherapy with T cells stably and transiently expressing anti-EpCAM CAR in xenograft models of peritoneal carcinomatosis" Oncotarget, 2017; vol. 8(8); pp. 13545-13559.
Shirasu et al. "Molecular Characterization of a Fully Human Chimeric T-Cell Antigen Receptor for Tumor-Associated Antigen EpCAM" J Biomed Biotechnol. 2012; vol. 2012:853879. 7 pages.
Zhang et al. "Akt inhibition at the initial stage of CAR-T preparation enhances the CAR-positive expression rate, memory phenotype and in vivo efficacy" Am J Cancer Res.; Nov. 2019; vol. 9(11); pp. 2379-2396.

* cited by examiner

*Primary Examiner* — Marianne P Allen
(74) *Attorney, Agent, or Firm* — Perkins Coie LLP; Viola Kung

(57) ABSTRACT

The present invention is directed to a humanized monoclonal anti-human EpCAM antibody, such as a single-chain variable fragment (scFv), comprising $V_H$ having the amino acid of SEQ ID NO: 2 and $V_L$ having the amino acid of SEQ ID NO: 4. The present invention is also directed to a chimeric antigen receptor fusion protein comprising from N-terminus to C-terminus: (i) a single-chain variable fragment (scFv) of the present invention, (ii) a transmembrane domain, (iii) at least one co-stimulatory domains, and (iv) an activating domain.

10 Claims, 15 Drawing Sheets
Specification includes a Sequence Listing.

EPCAM ANTIBODY AND EPCAM-CAR-T CELLS

This application is a continuation of PCT/US2020/014999, filed Jan. 24, 2020; which claims the priority of U.S. Provisional Application No. 62/796,975, filed Jan. 25, 2019. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Jan. 22, 2020, and a size of 18964 bytes. The Sequence Listing filed via EFS-Web is part of the specification and is hereby incorporated in its entirety by reference herein.

FIELD OF THE INVENTION

The present invention relates to humanized EpCAM antibody and EpCAM-CAR-T Cells, which are useful in the field of adoptive immunity gene therapy for tumors.

BACKGROUND OF THE INVENTION

Immunotherapy is emerging as a highly promising approach for the treatment of cancer. T cells or T lymphocytes, the armed forces of our immune system, constantly look for foreign antigens and discriminate abnormal (cancer or infected cells) from normal cells. Genetically modifying T cells with CAR (Chimeric antigen receptor) constructs is the most common approach to design tumor-specific T cells. CAR-T cells targeting tumor-associated antigens (TAA) can be infused into patients (called adoptive cell transfer or ACT) representing an efficient immunotherapy approach [1, 2]. The advantage of CAR-T technology compared with chemotherapy or antibody is that reprogrammed engineered T cells can proliferate and persist in the patient ("a living drug")[1, 2].

CARs usually consist of a monoclonal antibody-derived single-chain variable fragment (scFv) at the N-terminal part, hinge, transmembrane domain and a number of intracellular co-activation domains: (i) CD28, (ii) CD137 (4-1BB), CD27 or other co-stimulatory domains, in tandem with a activation CD3-zeta domain. (FIG. 1) [3]. The evolution of CARs went from first generation (with no co-stimulation domains) to second generation (with one co-stimulation domain) to third generation CAR (with several co-stimulation domains). Generating CARs with multiple costimulatory domains (the so-called $3^{rd}$ generation CAR) have led to increased cytolytic CAR-T cell activity, improved persistence of CAR-T cells leading to its augmented antitumor activity.

FIG. 1 illustrates the structures of CAR. The left panel shows the structure of the first generation of CAR (no costimulatory domains). The middle panel shows the structure of the second generation of CAR (one co-stimulation domain). The right panel shows the third generation of CAR (two or several co-stimulation domains) [3].

EpCAM

EpCAM (Epithelial Cell Adhesion Molecule) (CD326) antigen is a 39-40 kDa cell surface glycoprotein that is encoded by EpCAM gene. EpCAM plays a crucial role in cell adhesion, growth, proliferation, inflammation, cancer and metastasis. It is highly overexpressed in many types of tumors: 35.6%—in breast cancer; 69%—in ovarian cancer; 86%—in non-small lung cancer; >86% in colorectal cancer. EpCAM is expressed in many normal tissues but its expression in tumor tissues is significantly higher. Targeting EpCAM was recently demonstrated with siRNA, monoclonal anti-EpCAM antibodies, bi-specific antibodies, and CAR-T cells.

The human EpCAM protein consists of 314 amino acids: 24-265, extracellular domain; 266-288, transmembrane domain; 289-314, cytoplasmic domain. EpCAM is involved in WNT, ERK, AKT survival signaling, and plays role in motility, proliferation and cell growth. EpCAM is also a marker of circulating tumor cells and cancer stem cells.

DETAILED DESCRIPTION OF THE INVENTION

Definitions

Figure 1:
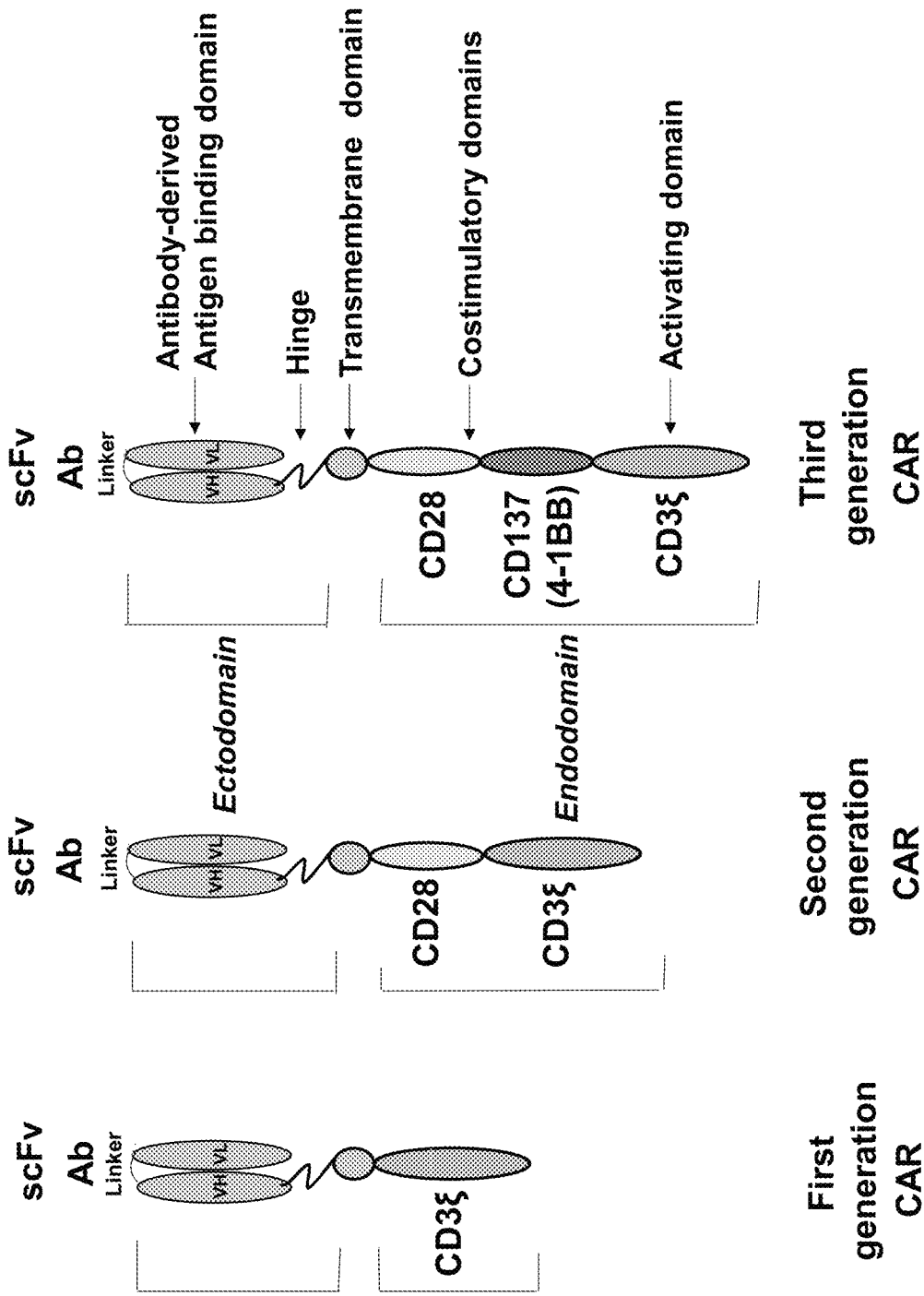
FIG. 1 illustrates the structures of CAR. The left panel shows the structure of the first generation of CAR (no costimulatory domains). The middle panel shows the structure of the second generation of CAR (one co-stimulation domain). The right panel shows the third generation of CAR (two or several co-stimulation domains) [3].

As used herein, a "chimeric antigen receptor (CAR)" is a receptor protein that has been engineered to give T cells the new ability to target a specific protein. The receptor is chimeric because they combine both antigen-binding and T-cell activating functions into a single receptor. CAR is a fused protein comprising an extracellular domain capable of binding to an antigen, a transmembrane domain, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, "CDR"s are complementary-determining Regions of VH or VL chains of antibody which are critical for binding with antigen.

As used herein, a "domain" means one region in a polypeptide which is folded into a particular structure independently of other regions.

As used herein, "humanized antibodies" are antibodies derived from non-human species whose protein sequences have been modified to increase their similarity to antibody variants produced naturally in humans. For example, after a mouse antibody is developed, the DNA coding for that antibody can be sequenced. The DNA sequence corresponding to the antibody CDRs can then be determined. The CDR sequences can be inserted into a construct containing the DNA for a human antibody variant to prepare humanized antibodies.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for engineering an scFv are known to a person skilled in the art.

As used herein, a "tumor antigen" means a biological molecule having antigenecity, expression of which causes cancer.

The inventors have engineered humanized EpCAM scFv starting from heavy and light chain variable regions of mouse monoclonal antibody derived from hybridoma cell line AUA1 Ab [4, 5]. The inventors have produced EpCAM-CAR-T cells based on humanized EpCAM antibody to target cancer cells overexpressing EpCAM tumor antigen. The EpCAM-CAR-T cells of the present invention have high cytotoxic activity against several cancer cell lines The present invention is directed to a humanized anti-human EpCAM antibody comprising $V_H$ having the amino acid of SEQ ID NO: 2 and $V_L$ having the amino acid of SEQ ID NO: 4.

In one embodiment, the humanized anti-human EpCAM antibody is a single-chain variable fragment (scFv). ScFv can be $V_H$-linker-$V_L$ or $V_L$-linker-$V_H$.

The present invention is also directed to a chimeric antigen receptor fusion protein comprising from N-terminus to C-terminus: (i) a single-chain variable fragment (scFv) against EpCAM in which $V_H$ has the amino acid sequence of SEQ ID NO:2, and $V_L$ has the amino acid of SEQ ID NO: 4, (ii) a transmembrane domain, (iii) at least one co-stimulatory domains, and (iv) an activating domain.

Figure 2:
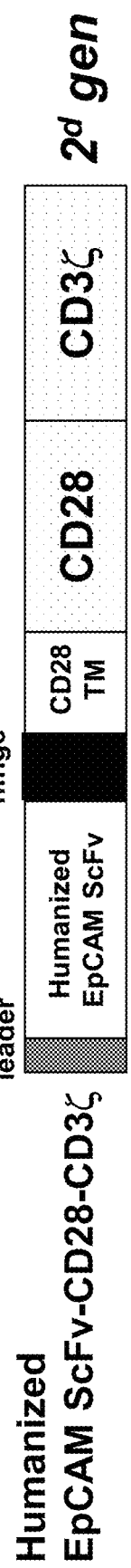
FIG. 2 shows the structure of EpCAM CAR construct. The second generation CAR is used.

In one embodiment, the CAR structure is shown in FIG. 2.

In one embodiment, the co-stimulatory domain is selected from the group consisting of CD28, 4-1BB, GITR, ICOS-1, CD27, OX-40 and DAP10. A preferred the co-stimulatory domain is CD28 or 4-1BB.

A preferred activating domain is CD3 zeta (CD3 Z or CD3ζ).

The transmembrane domain may be derived from a natural polypeptide, or it may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3ε., CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. Optionally, a short oligopeptide linker or a polypeptide linker, for example, a linker having a length of 2 to 10 amino acids can be arranged between the transmembrane domain and the intracellular domain. In one embodiment, a linker sequence having a glycine-serine continuous sequence can be used.

The present invention provides a nucleic acid encoding the EpCAM-CAR. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBank for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

A nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. A virus vector lacking the replicating ability so as not to self-replicate in an infected cell is preferably used.

For example, when a retrovirus vector is used, a suitable packaging cell based on a LTR sequence and a packaging signal sequence possessed by the vector can be selected for preparing a retrovirus particle using the packaging cell. Examples of the packaging cell include PG13 (ATCC CRL-10686), PA317 (ATCC CRL-9078), GP+E-86 and GP+envAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

A CAR-T cell binds to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage.

The cell expressing the CAR can be used as a therapeutic agent for a disease. The therapeutic agent comprises the cell expressing the CAR as an active ingredient, and it may further comprise a suitable excipient.

The inventors have generated a humanized anti-human EpCAM antibody and characterized it. The present humanized anti-human EpCAM antibody exhibits selective and high-affinity binding to human EpCAM, and it is used to construct a single-chain variable fragment (scFv). The inventors insert the EpCAM scFv into a second-generation CAR to generate CAR-T cells. EpCAM-CAR-T cells express higher cytotoxic activity against EpCAM-positive cancer cells than against non-transduced T cells and Mock-CAR-T cells.

The humanized EpCAM-CAR-T cells of the present invention secret high levels of IFN-gamm against EpCAM-positive cancer cells; they are positive by cytotoxicity assay against target cancer cells with EpCAM overexpression. The inventors demonstrate that humanized EpCAM-CAR-T cells significantly decreased colon tumor growth in a mouse xenograft model, which indicates EpCAM-CAR-T cells can treat patients with EpCAM positive tumors.

The advantages of the humanized EpCAM monoclonal antibody or EpCAM-ScFv of the present invention over mouse EpCAM ScFv (AUA1 antibody) include less immunogenicity to human due to humanized EpCAM scFv. The humanized EpCAM scFv are more cytotoxic against cancer cells than CAR-T cells with mouse ScFv. The EpCAM humanized antibody is highly potent as a therapeutic agent for CAR-T and other uses in many clinical applications.

The present humanized EpCAM ScFv can be used for immunotherapy applications: toxin/drug-conjugated antibody, monoclonal therapeutic antibody, and CAR-T cell immunotherapy.

Humanized EpCAM-CAR-T cells using the present humanized EpCAM ScFv effectively target EpCAM antigen in EpCAM-positive cancer cell lines such as ovarian, colon, pancreatic, melanoma, cervical cancer, and other EpCAM-positive cancers.

Humanized EpCAM-CAR-T cells can be used in combination with different chemotherapy: checkpoint inhibitors, targeted therapies, small molecule inhibitors, and antibodies.

Humanized EpCAM-CAR-T cells can be used clinically for EpCAM-positive cancer cells.

Modifications of co-activation domains such as CD28, 4-1BB and others can be used to increase the efficacy of CAR-T cells. Tag-conjugated humanized EpCAM scFv can be used for CAR generation.

Humanized EpCAM-CAR-T cells can be used with different safety switches such as t-EGFR, RQR (Rituximab-CD34-Rituximab), inducible caspase-9 and other.

Third generation CAR-T or other co-activation signaling domains can be used with humanized EpCAM-scFv to prepare EpCAM-CAR-T.

The humanized EpCAM CAR can be combined with CARs targeting other tumor antigens or tumor microenvironment, e.g., VEGFR-1-3, PDL-1. Bi-specific antibodies with EpCAM and CD3, or other antigens can be generated for therapy.

The humanized EpCAM-CAR can be used for generating other types of cells such as CAR-natural killer (NK) cells, EpCAM-CAR-macrophages, and EpCAM-CAR hematopoietic cells, which can target EpCAM-positive cancers.

The present invention provides T cells, NK cells, macrophages, or hematopoietic cells, modified to express the EpCAM-CAR.

EpCAM-CAR-T cells can be used against cancer stem cells and circulating tumor stem cells that are most resistant against chemotherapy and form aggressive tumors.

EpCAM-NK cells EpCAM-macrophages can be used for targeting different types of cancer EpCAM-CAR-T cells can be delivered intra-tumorally to patients for increased safety.

The following examples further illustrate the present invention. These examples are intended merely to be illustrative of the present invention and are not to be construed as being limiting.

EXAMPLES

Example 1

Humanized EpCAM VII, VL and scFv Sequences

EpCAM scFv was derived from mouse hybridoma clones (AUA1 [4, 5]). The sequences of heavy and light chain variable regions of mouse clone AUA1 were determined and were used to construct a humanized scFv. The humanization was done as described in Golubovskaya et al (3). The structure of EpCAM scFv is: VH-linker-VL.

The bold highlights the nucleotide sequence of $V_H$; the underlined highlights the PGP-21,DNA,M nucleotide sequence of $V_L$; in between (italicized) is the nucleotide sequence encoding a linker.

```
                                               (SEQ ID NO: 1)
caggtgcagctggtgcagagcggcagcgaactgaaaaaaccgggcgcgag cgtgaaagtgagctgcaaagcgagcggctataccttaccaactatggca tgaactgggtgcgccaggcgccgggccagggcctggaatggatgggctgg attaacacctataccggcgaaccgacctatgcggatgattttaaaggccg ctttgtgtttagcctggataccagcgtgagcaccgcgtatctgcagatta gcagcctgaaagcggaagataccgcggtgtattattgcgcgcgctggctg cgcgatttgattattggggcgcgggcaccaccgtgaccgtgagcagc

GGT GGC GGA GGT TCT GGA GGC GGT GGT TCA GGT GGC

GGT GGT TCC gaaattgtgctgacccagagcccggcgaccctgagcctgagcccgggcga acgcgcgacccctgagctgcagcgcgagcagcagcattagctatatgcatt ggtatcagcagaaaccgggccaggcgccgcgcctgctgatttatgatacc agcaaactggcgaccggcattccggcgcgctttagcggcagcggcagcgg caccgatttacccctgaccattagcagcctggaaccggaagattttgcgg tgtattattgccatcagcgcagcagctatccgtatacattggcggcggca ccaaactggaaattaaa
```

-continued

V_H amino acid sequence
(SEQ ID NO: 2)
QVQLVQSGSELKKPGASVKVSCKASGYTFTNYGMNWVRQAPGQGLEWMGW

INTYTGEPTYADDFKGRFVFSLDTSVSTAYLQISSLKAEDTAVYYCARWL

RDFDYWGAGTTVTVSS

Linker amino acid sequence
(SEQ ID NO: 3)
GGGGSGGGGSGGGGS

V_L amino acid sequence
(SEQ ID NO: 4)
EIVLTQSPATLSLSPGERATLSCSASSSISYMHWYQQKPGQAPRLLIYDT

SKLATGIPARFSGSGSGTDFTLTISSLEPEDFAVYYCHQRSSYPYTFGGG

TKLEIK

Humanized EpCAM scFv Protein
(SEQ ID NO: 5)
QVQLVQSGSELKKPGASVKVSCKASGYTFTNYGMNWVRQAPGQGLEWMGW

INTYTGEPTYADDFKGRFVFSLDTSVSTAYLQISSLKAEDTAVYYCARWL

RDFDYWGAGTTVTVSSGGGGSGGGGS

Example 2

Humanized EpCAM-CAR Sequences with CD28 as a Co-Stimulating Domain

Figure 3:
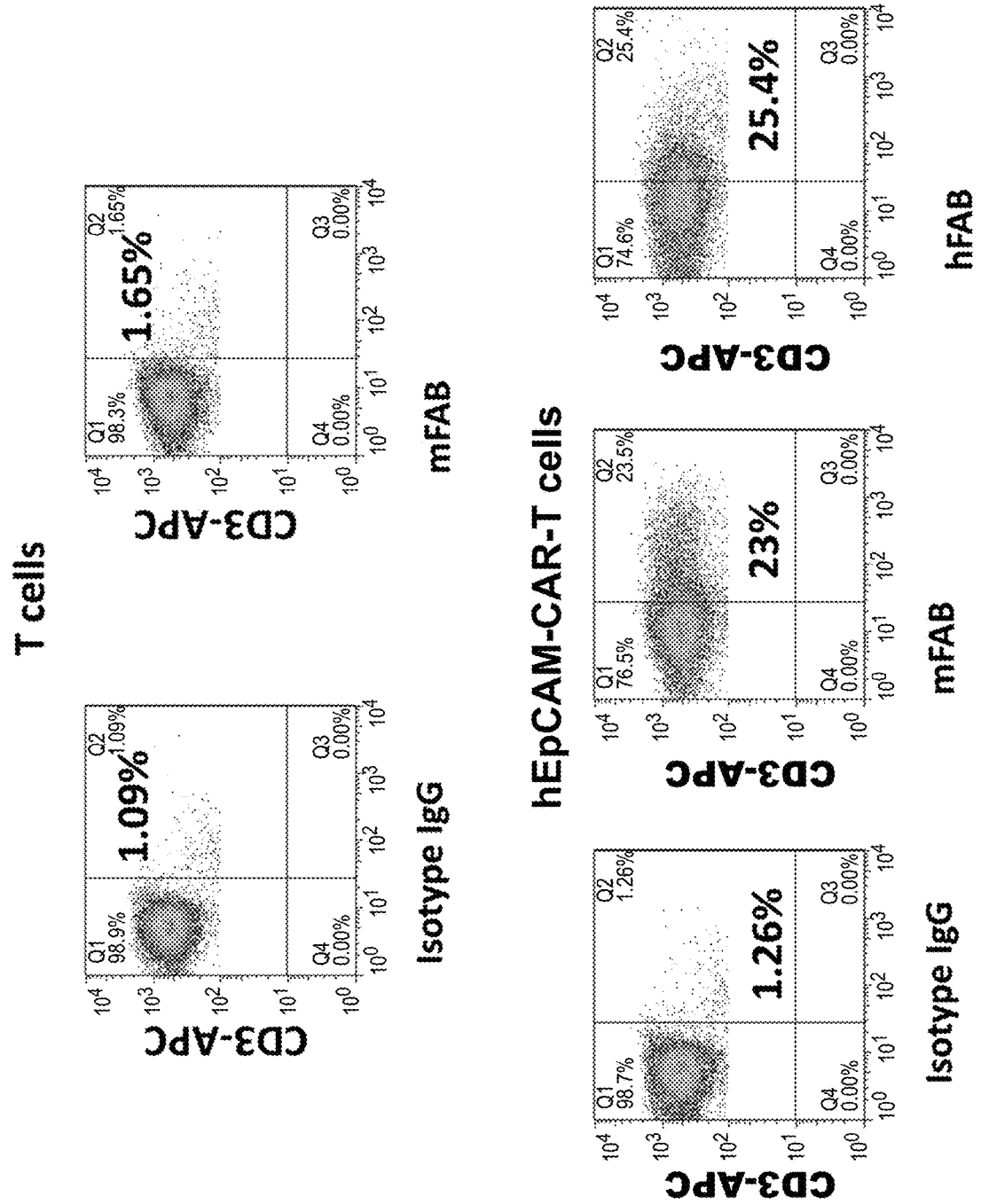
FIG. 3 shows that 25.4% of humanized EpCAM-CAR-T cells (CD28 co-stimulating, Example 2, PMC 306) were positive against anti-human $F(ab)_2$, and 23% of humanized EpCAM-CAR-T cells were positive against anti-mouse $F(ab)_2$.

The scheme of EpCAM-CAR construct is shown on FIG. 3.

The following nucleotide sequence shows EpCAM ScFv-CD8 hinge-TM28-CD28-CD3 zeta of the present invention. The structure includes Human CD8 signaling peptide, EpCAM scFv (V_H-Linker-V_L), CD8 hinge, CD28 transmembrane domain, CD28 co-stimulating domain CD3 zeta activation domain (FIG. 2).

EpCAM scFv (V_H-Linker-V_L)-CD8 Hinge-CD28 TM-CD28-CD3-Zeta:

<CD8 leader>
Nucleotide
(SEQ ID NO: 6)
ATGGCCTTACCAGTGACCGCCTTGCTCCTGCCGCTGGCCTTGCTGCTCCA

CGCCGCCAGGCCG

Amino Acid
(SEQ ID NO: 7)
MALPVTALLLPLALLLHAARP

<Nhe I Restriction Site>

GCTAGC <AS>

<EpCAM scFV>

VH-linker-VL, see Example 1 for nucleic acid sequences and amino acid sequences.

<Xho I Restriction Site>

CTCGAG <LE>

<aagccc><KP>

<CD8 Hinge>

Nucleotide
(SEQ ID NO: 8)
ACCACGACGCCAGCGCCGCGACCACCAACACCGGCGCCCACCATCGCGTC

GCAGCCCCTGTCCCTGCGCCCAGAGGCGAGCCGGCCAGCGGCGGGGGGCG

CAGTGCACACGAGGGGGCTGGACTTCGCCAGTGAT

Amino Acid
(SEQ ID NO: 9)
TTTPAPRPPTPAPTIASQPLSLRPEASRPAAGGAVHTRGLDFASD

<CD28 Transmembrane >

Nucleotide
(SEQ ID NO: 10)
TTTTGGGTGCTGGTGGTGGTTGGTGGAGTCCTGGCTTGCTATAGCTTGCT

AGTAACAGTGGCCTTTATTATTTTCTGGGTG

Amino Acid
(SEQ ID NO: 11)
FWVLVVVGGVLACYSLLVTVAFIIFWV

<CD28 Co-Stimulatory>

Nucleotide
(SEQ ID NO: 12)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC

Amino acid
(SEQ ID NO: 13)
RSKRSRLLHSDYMNMTPRRPGPTRKHYQPYAPPRDFAAYRS

<CD3 Zeta>

Nucleotide
(SEQ ID NO: 14)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGCAG

AGAAGGAAGAACCCTCAGGAAGGCCTGTACAATGAACTGCAGAAAGATAA

GATGGCGGAGGCCTACAGTGAGATTGGGATGAAAGGCGAGCGCCGGAGGG

GCAAGGGGCACGATGGCCTTTACCAGGGTCTCAGTACAGCCACCAAGGAC

ACCTACGACGCCCTTCACATGCAGGCCCTGCCCCCTCGCTAA

Amino acid
(SEQ ID NO: 15)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

<EcoRI Restriction Site>
Gaattc

Translated amino-acid sequence of EpCAM-CAR protein (PMC376, SEQ ID NO: 16) is shown below V_H in bold, linker in italics, V_L is underlined.

```
MALPVTALLLPLALLLHAARPASQVQLVQSGSELKKPGASVKVSCKASGY

TFTNYGMNWVRQAPGQGLEWMGWINTYTGEPTYADDFKGRFVFSLDTSVS

TAYLQISSLKAEDTAVYYCARWLRDFDYWGAGTTVTVSSGGGGSGGGGSG

GGGSEIVLTQSPATLSLSPGERATLSCSASSSISYMHWYQQKPGQAPRLL

IYDTSKLATGIPARFSGSGSGTDFTLTISSLEPEDFAVYYCHQRSSYPYT

FGGGTKLEIKLEKPTTTPAPRPPTPAPTIASQPLSLRPEASRPAAGGAVH

TRGLDFASDKPFWVLVVVGGVLACYSLLVTVAFIIFWVRSKRSRLLHSDY

MNMTPRRPGPTRKHYQPYAPPRDFAAYRSRVKFSRSADAPAYQQGQNQLY

NELNLGRREEYDVLDKRRGRDPEMGGKPQRRKNPQEGLYNELQKDKMAEA

YSEIGMKGERRRGKGHDGLYQGLSTATKDTYDALHMQALPPR
```

Example 3

Humanized EpCAM-CAR Sequences with 4-1BB as a Co-Stimulating Domain

In this example, the humanized EpCAM-CAR sequences are identical to those described in Example 2, except 4-1BB was used as a costimulatory domain instead of CD28.
<41BB Costimulatory Domain>

```
Nucleotide
                               (SEQ ID NO: 17)
Aaacggggcagaaagaaactcctgtatatattcaaacaaccatttatgag accagtacaaactactcaagaggaagatggctgtagctgccgatttccag aagaagaagaaggaggatgtgaactg Amino acid
                               (SEQ ID NO: 18)
KRGRKKLLYIFKQPFMRPVQTTQEEDGCSCRFPEEEEGGCEL CAR Amino Acid Sequence
                        (PMC 710, SEQ ID NO: 19)
MALPVTALLLPLALLLHAARPASQVQLVQSGSELKKPGASVKVSCKASGY

TFTNYGMNWVRQAPGQGLEWMGWINTYTGEPTYADDFKGRFVFSLDTSVS

TAYLQISSLKAEDTAVYYCARWLRDFDYWGAGTTVTVSSGGGGSGGGGSG

GGGSEIVLTQSPATLSLSPGERATLSCSASSSISYMHWYQQKPGQAPRLL

IYDTSKLATGIPARFSGSGSGTDFTLTISSLEPEDFAVYYCHQRSSYPYT

FGGGTKLEIKLEKPTTTPAPRPPTPAPTIASQPLSLRPEASRPAAGGAVH

TRGLDFASDKPFWVLVVVGGVLACYSLLVTVAFIIFWVKRGRKKLLYIFK

QPFMRPVQTTQEEDGCSCRFPEEEEGGCELRVKFSRSADAPAYQQGQNQL

YNELNLGRREEYDVLDKRRGRDPEMGGKPQRRKNPQEGLYNELQKDKMAE

AYSEIGMKGERRRGKGHDGLYQGLSTATKDTYDALHMQALPPR
```

Example 4

CAR Lentivirus Production

The inventors generated humanized EpCAM-ScFv-CAR constructs and cloned them inside lentiviral vectors either with promoter EF1 and CD28 costimulatory domain for PMC376 or with MNDU3 promoter and 41BB costimulatory domain for PMC710.

Lentiviruses were generated in 293T cells by the standard procedure as described in [6]; the titers were established by real time PCR.

Example 5

Peripheral Blood Mononuclear Cell (PBMC) Isolation from Whole Blood

Whole blood (Stanford Hospital Blood Center, Stanford, CA) was collected from individual or mixed donors (depending on the amount of blood required) in 10 mL Heparin vacutainers (Becton Dickinson). Approximately 10 ml of whole anti-coagulated blood was mixed with sterile phosphate buffered saline (PBS) buffer for a total volume of 20 ml in a 50 ml centrifuge tube (PBS, pH 7.4, without $Ca^{+2}$ and $Mg^{+2}$). The blood/PBS (20 ml) was layered on top of 15 mL of Ficoll-Paque PLUS (GE Healthcare) in a conical centrifuge tube gently, and the sample was centrifuged at 400×g for 30-40 min at room temperature. The layer of cells containing peripheral blood mononuclear cells (PBMC) at the diluted plasma/Ficoll interface was removed, washed, and centrifuged at 200×g for 10 min at room temperature. Cells were counted with a hemocytomter. The PBMC were washed once with CAR-T media (AIM V-AlbuMAX(BSA) (Life Technologies), with 5% AB serum and 1.25 µg/mL amphotericin B (Gemini Bioproducts, Woodland, CA), 100 U/mL penicillin, and 100 µg/mL streptomycin) and used for experiments or were frozen at −80° C.

Example 6

T-Cell Activation from PBMC

The isolated PBMC cells are resuspended in CAR-T medium with 300 U/mL huIL2 (from a 1000× stock; Invitrogen) and mixed with CD3-CD28 beads at a 1:1 bead-to-cell ratio. The cells are incubated at 37° C. in the presence of $CO_2$ for 24 hours before viral transduction.

Example 7

T-Cell Transduction and Expansion

Following activation of PBMC, cells were incubated for 24 hours at 37° C., 5% $CO_2$. To each well of 1×10⁶ cells, 5×10⁶ lentivirus and 2 µL/mL of media of Transplus (Alstem, Richmond, CA) (a final dilution of 1:500) were added. Cells were incubated for an additional 24 hours before repeating the addition of virus. Cells were then grown in the continued presence of 300 U/ML of IL-2 fresh medium with IL-2 for a period of 12-14 days (total incubation time was dependent on the final umber of CAR-T cells required). Cells concentrations were analyzed every 2-3 days, with media being added at that time to dilute the cell suspension to 1×10⁶ cells/mL.

Example 8

Transduction Verification by FACS Staining

Cells were washed and suspended in FACS buffer (phosphate-buffered saline (PBS) plus 0.1% sodium azide and 0.4% BSA), and then divided to 1×10⁶ aliquots.

Fc receptors were blocked with normal goat IgG (LifeTechnologies). 1.0 ml FACS buffer was added to each tube, mixed well and spun down at 300 g for 5 min.

Biotin-labeled polyclonal goat anti-mouse F(ab)$_2$ antibody or anti-human F(ab)$_2$ antibody (Life Technologies) was to detect EpCAM scFv; biotin-labeled normal polyclonal goat IgG antibodies (Life Technologies) was added to serve as an isotype control.

Cells were suspended in FACS buffer and blocked with normal mouse IgG (Invitrogen) by adding 100 µl 1:1000 diluted normal mouse IgG to each tube, and incubated on ice for 10 min. Cells were washed and re-suspended in 100 µl FACS buffer, and then stained with phycoerythrin (PE)-labeled streptavidin (BD Pharmingen, San Diego, CA) and allophycocyanin (APC)-labeled CD3 (eBiocience, San Diego, CA). Flow cytometry acquisition was performed with a BD FacsCalibur (BD Biosciences), and analysis was performed with FlowJo (Treestar, Inc. Ashland, OR).

FIG. 3 shows that transduced T cells with humanized EpCAM-CAR lentivirus (humanized EpCAM-CAR-T cells) had a detectable level of humanized anti-EpCAM scFv, which were detected by anti-mouse F(ab)$_2$ antibody or anti-human F(ab)$_2$ antibody (Jackson Immunoresearch; 109-066-097) [1:50]. 23% of humanized EpCAM-CAR-T cells (CD28 co-stimulating, Example 2, PMC 376 were positive against anti-mouse F(ab)$_2$, and 25.4% were positive against anti-human F(ab)$_2$.

Figure 4:
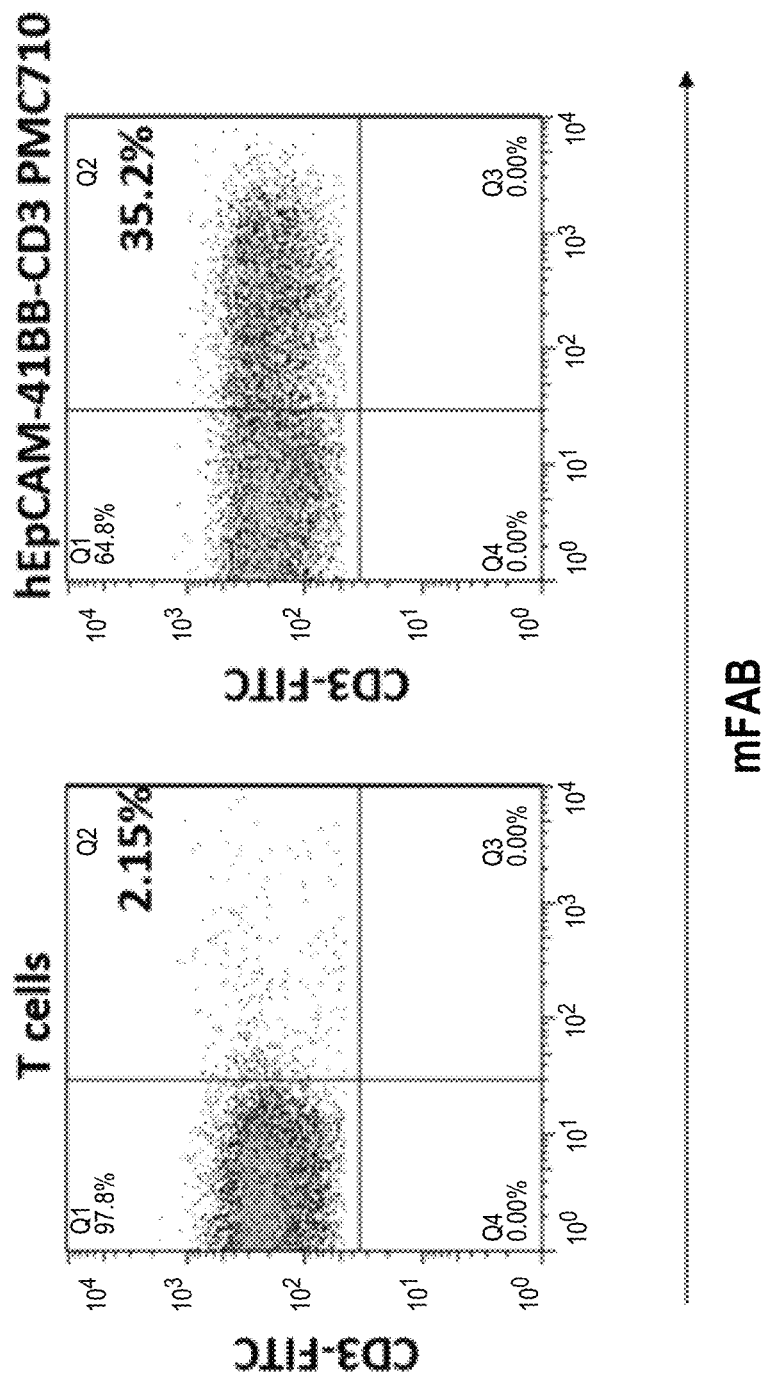
FIG. 4 shows that 35.2% of humanized EpCAM-CAR-T cells (4-1BB co-stimulating, Example 3, PMC 710) were positive against anti-mouse $F(ab)_2$.

FIG. 4 shows that 35.2% of humanized EpCAM-CAR-T cells (4-1BB co-stimulating, Example 3 PMC 710) were positive against anti-mouse Fab.

Figure 5:
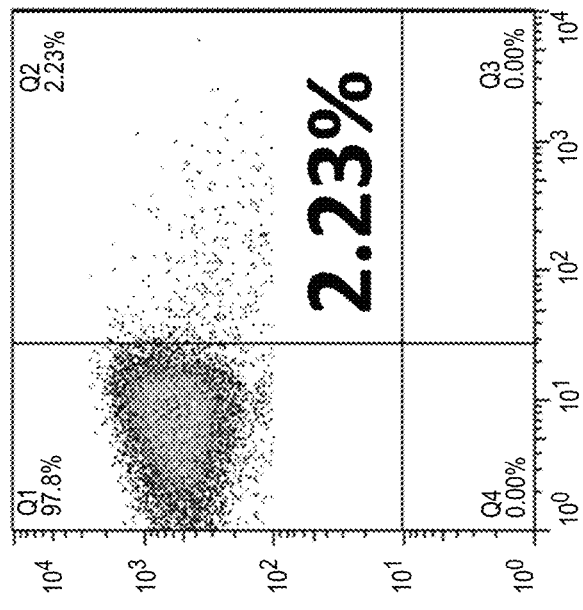
FIG. 5 shows that mouse EpCAM-CAR-T cells had a low expression of EpCAM, and only 2.23% of mouse EpCAM-CAR-T cells were detected by anti-mouse $F(ab)_2$.
Figure 5:
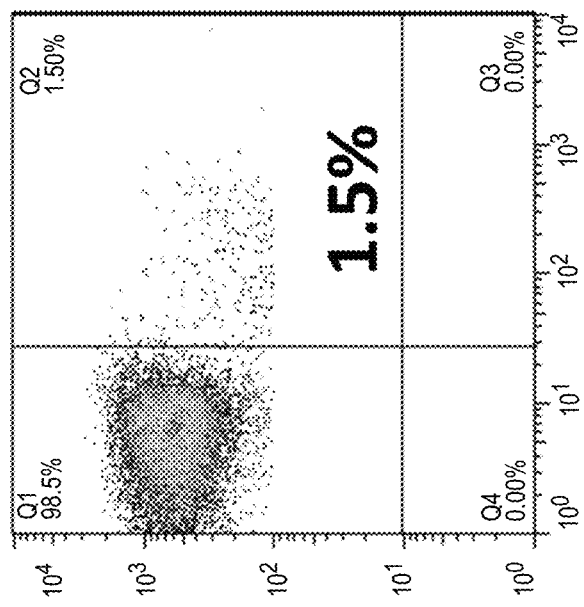

Mouse EpCAM-CAR-T cells were prepared according to Examples 2, and 4-7, except that mouse scFv sequences were generated from AUA1 mouse antibody. FIG. 5 shows that mouse EpCAM-CAR-T cells had a low expression of EpCAM, and only 2.23% of mouse EpCAM-CAR-T cells were detected by anti-mouse F(ab)$_2$.

Example 9

Cytotoxicity Assay of Humanized EpCAM-CAR-T Cells

The real-time cytotoxicity was performed using ACEA machine according to manufacturer's protocol. The cytotoxic activity of EpCAM-CAR-T cells (Example 2, CD28 cos-stimulating domain, PMC376) was tested against EpCAM-positive cancer cells of HT29 (colorectal adenocarcinoma, FIG. 6A), Lovo (colon cancer, FIG. 6B), OVCAR-3 (ovarian cancer, FIG. 6C), Hela (cervical cancer, FIG. 6D), and SKBR-3 (breast cancer, FIG. 6E).

Figure 6A:
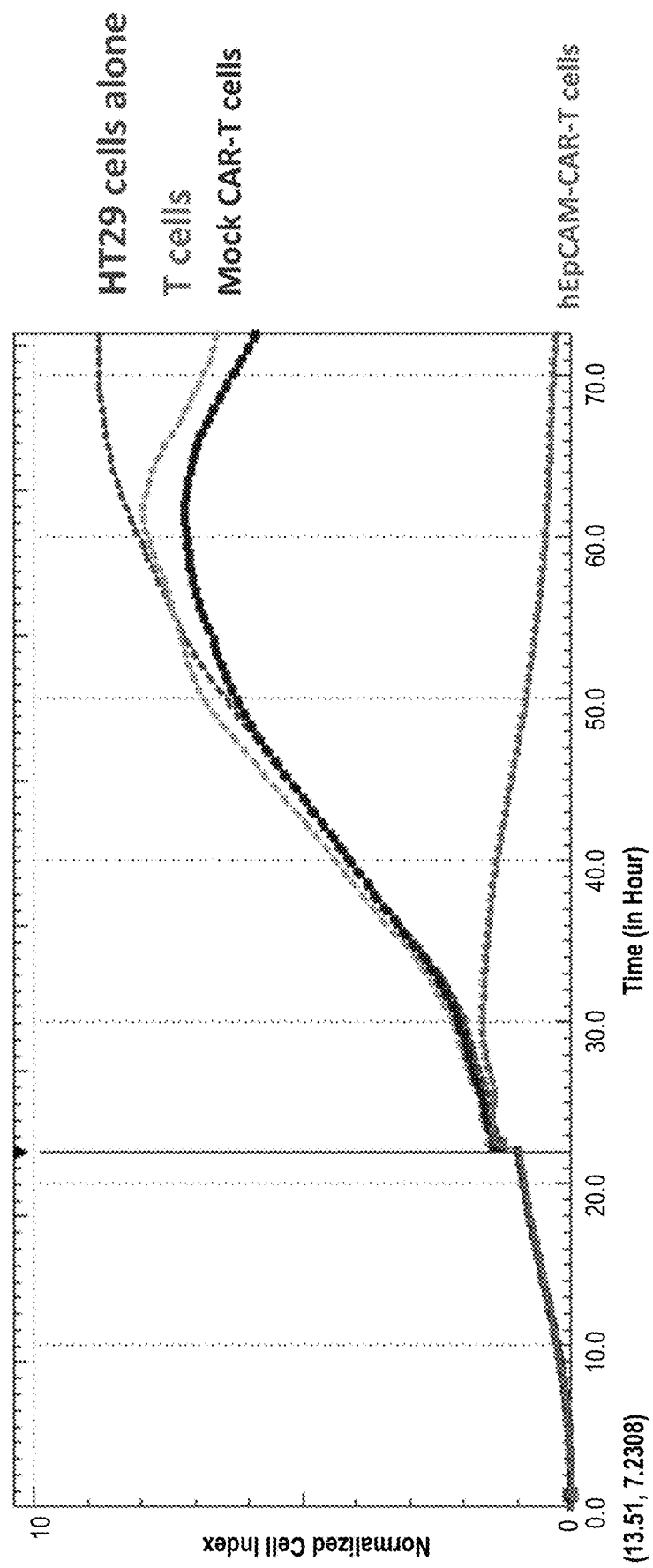
FIG. 6A demonstrates high cytotoxic activity of humanized EpCAM-CAR cells against colorectal cancer (HT29 cells).
Figure 6B:
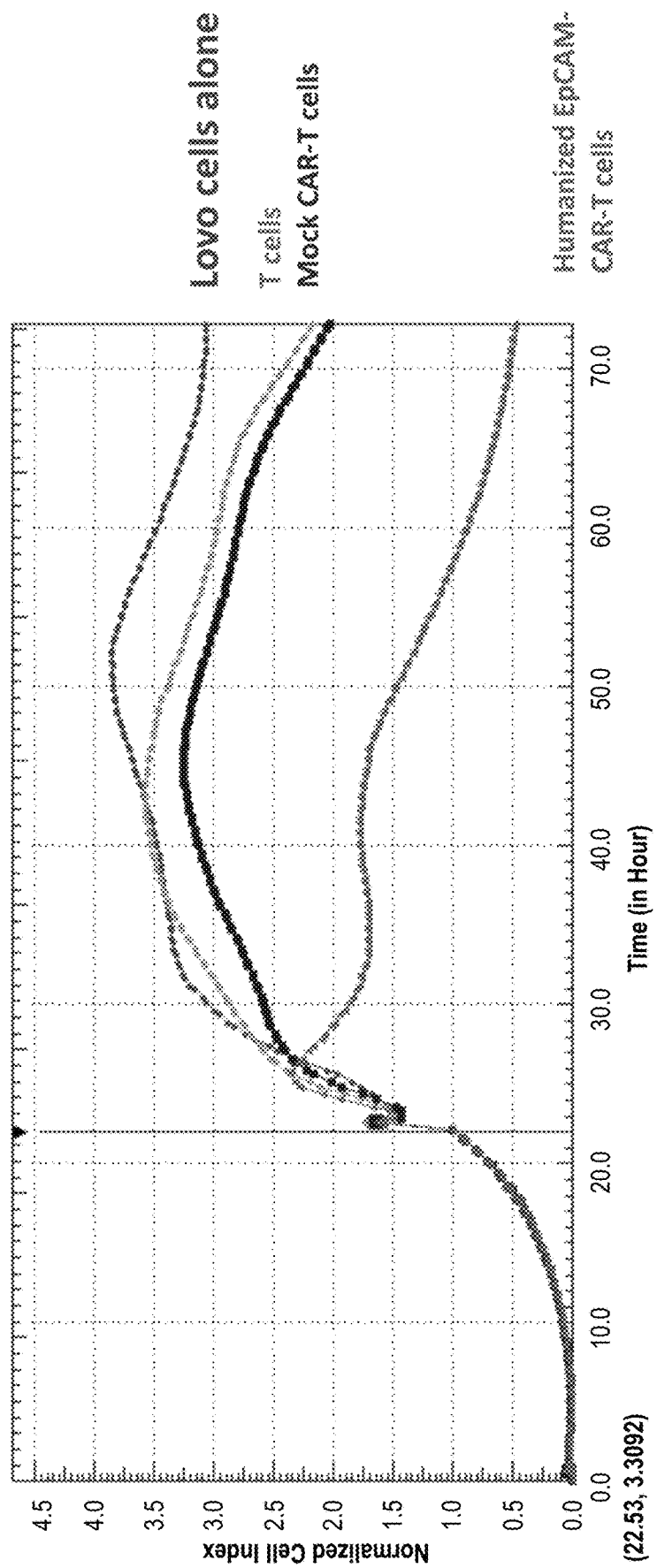
FIG. 6B demonstrates cytotoxic activity of humanized EpCAM-CAR cells against colon cancer (Lovo cells).
Figure 6C:
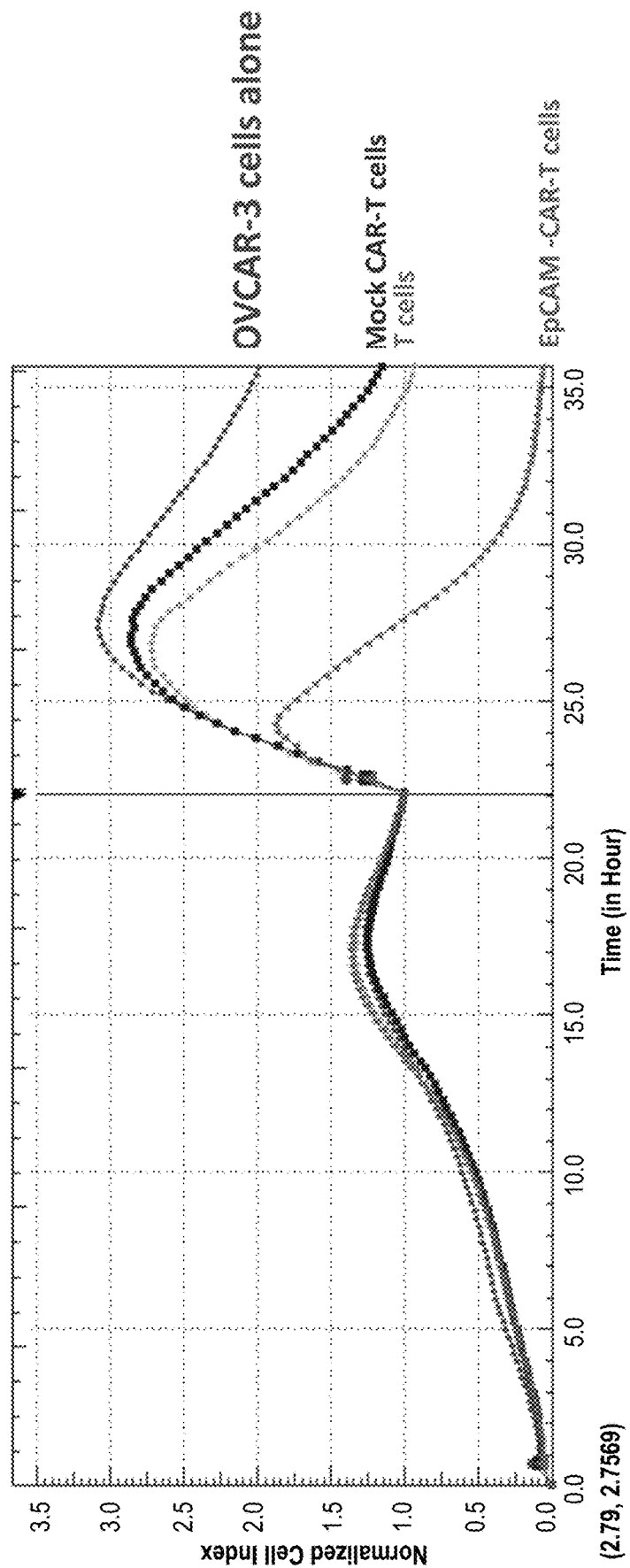
FIG. 6C demonstrates high cytotoxic activity of humanized EpCAM-CAR cells against ovarian cancer (OVCAR-3 cells).
Figure 6D:
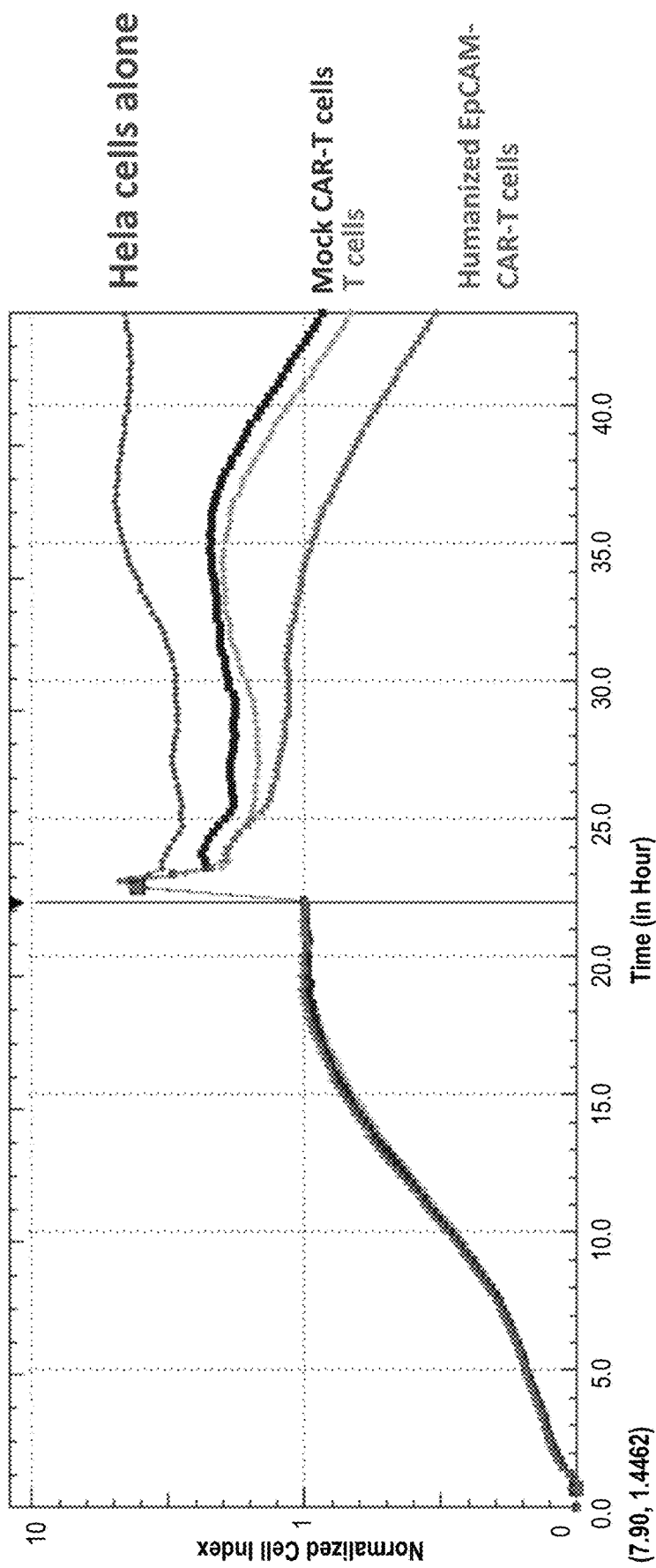
FIG. 6D demonstrates cytotoxic activity of humanized EpCAM-CAR cells against cervical cancer (Hela cells).
Figure 6E:
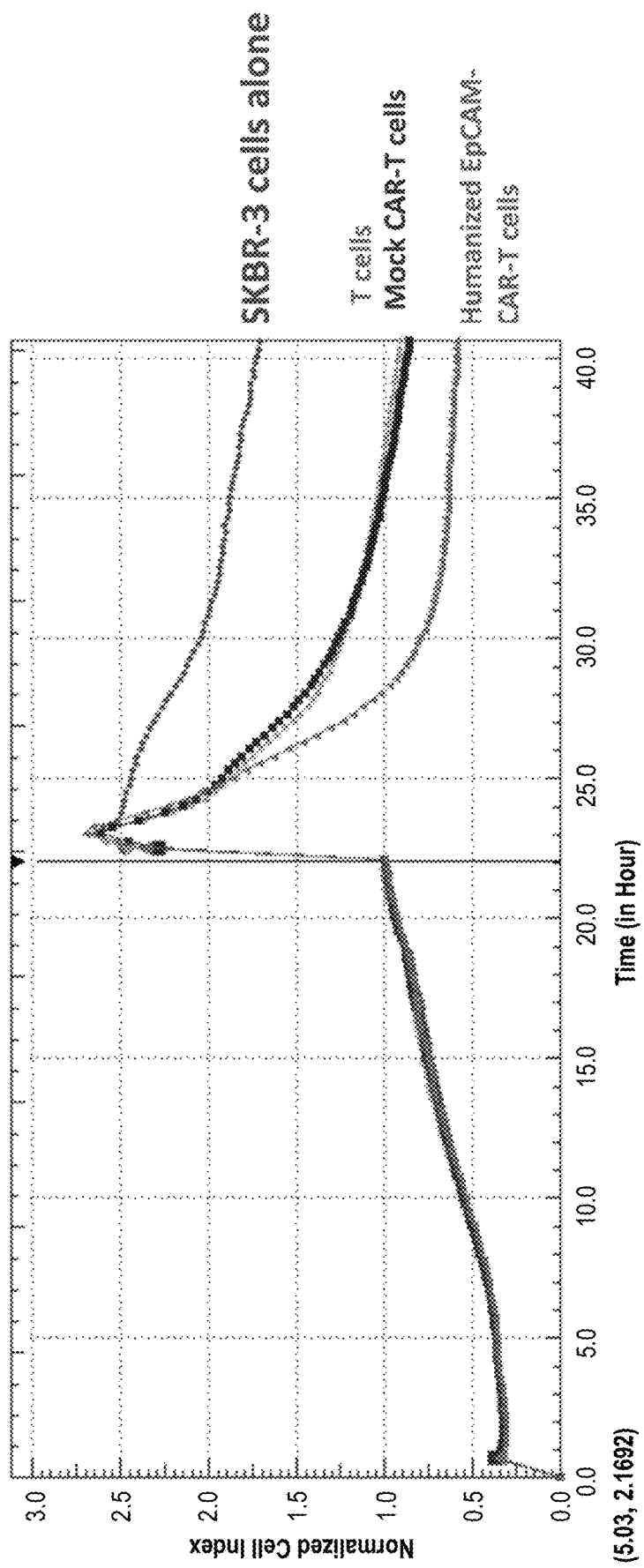
FIG. 6E demonstrates cytotoxic activity of humanized EpCAM-CAR cells against breast cancer (SKBR-3 cells).

The real-time cytotoxicity assay demonstrates high cytotoxic activity of EpCAM-CAR cells against colorectal cancer, colon cancer, and ovarian cancer (FIGS. 6A-6C). The cytotoxicities with EpCAM-CAR-T cells were lower in cervical and breast cancer cell line (FIG. 6D-6E). Hela and SKBR3 cells were reported to express less EpCAM.

The cytotoxic activity of EpCAM-CAR cells (Example 3, 4-1BB co-stimulating domain, PMC710) was also tested against Lovo cells (colon cancer). The results were similar to that of PMC376 in Lovo cells (data not shown).

Example 10

Cytotoxicity Assay (Comparison)

Figure 7:
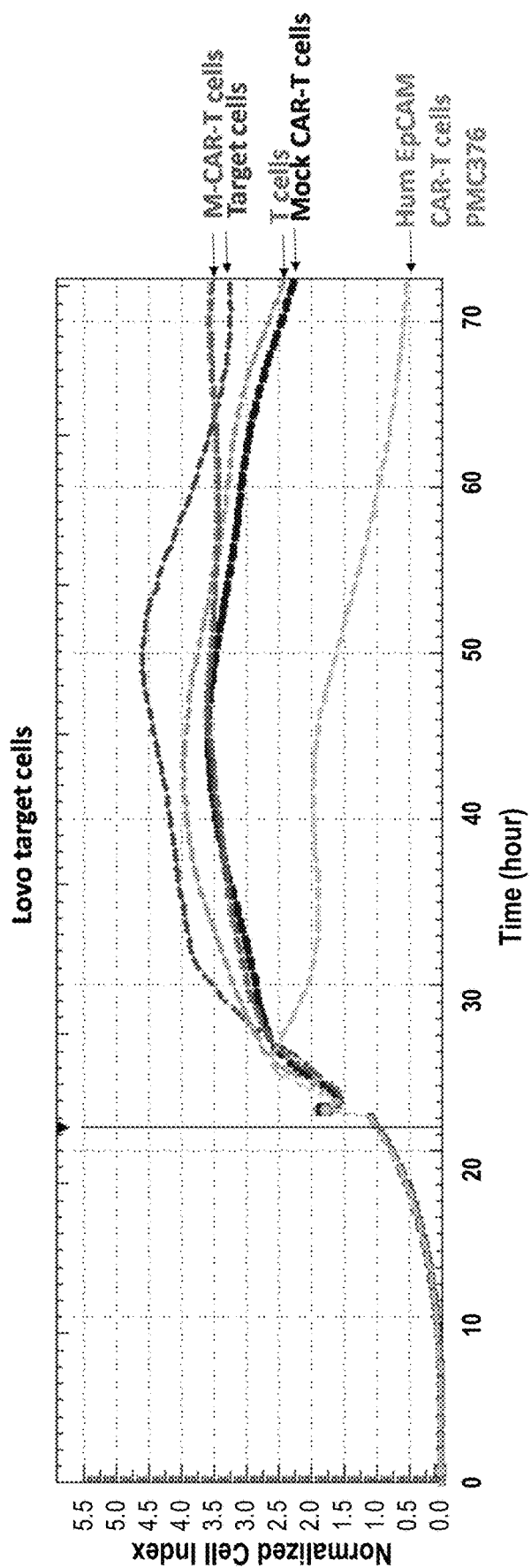
FIG. 7 compares the cytotoxicity of humanized EpCAM-CAR-T cells (PMC376) and mouse EpCAM-CAR-T cells in Lovo target cells.

The cytotoxicity of humanized EpCAM-CAR-T cells (PMC376) and mouse EpCAM-CAR-T cells were compared in Lovo target cells. The results are shown in FIG. 7. Due to low expression of mouse EpCAM CAR in CAR-T cells, mouse-CAR-T cells did not show cytotoxicity against Lovo cells, whereas humanized EpCAM-CAR-T cells had high cytotoxicity against Lovo cells.

Example 11

EpCAM-CAR Secreted High Level of IFN-Gamma Against EpCAM Positive Cancer Cells

Figure 8:
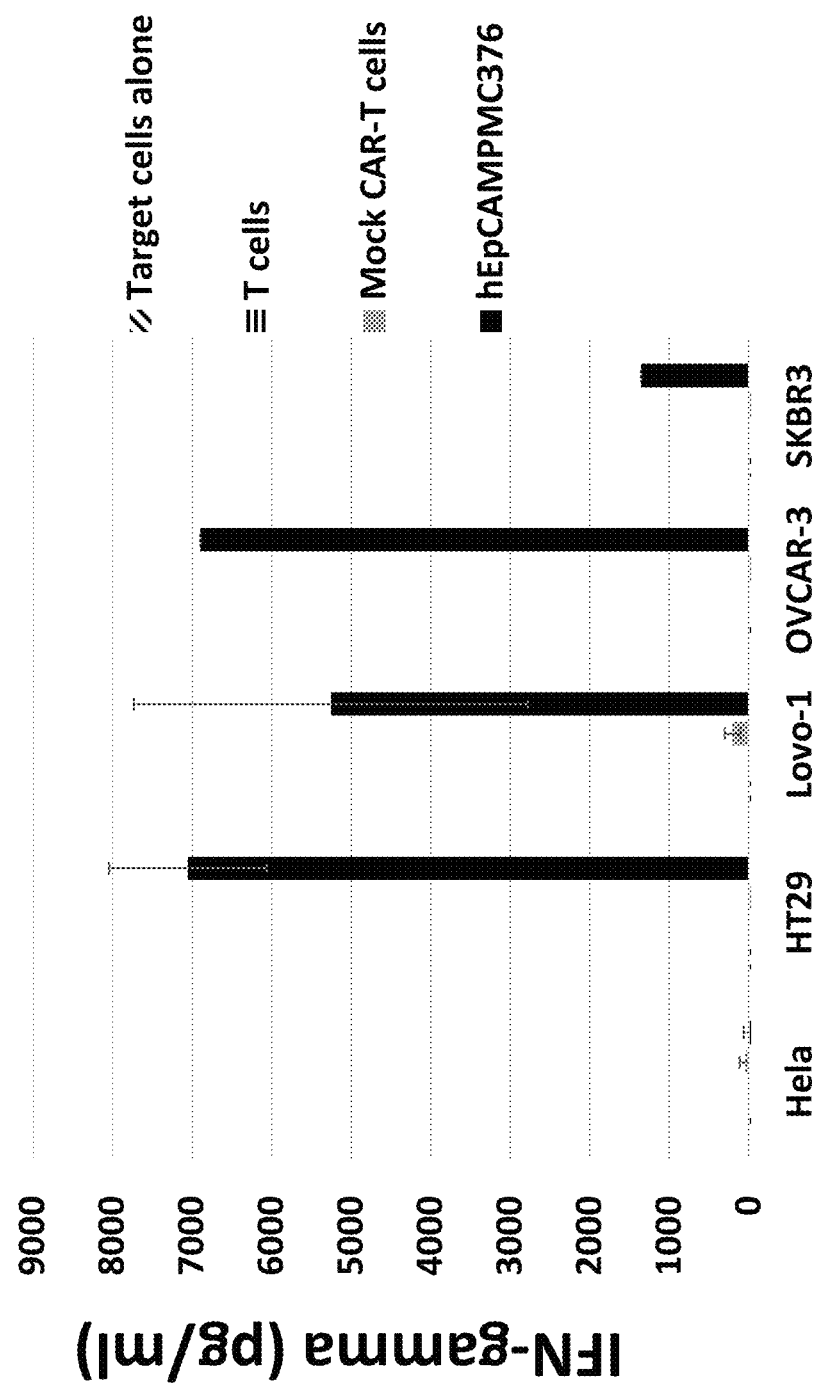
FIG. 8 shows that humanized EpCAM-CAR (PMC376) secreted high level of IFN-gamma against HT29, Lovo-1, OVCAR-3, and SKBR3 cells. Three independent experiments were done.

We collected supernatant of EpCAM-CAR-T incubated with cancer cells in RTCA assay and performed ELISA with kit from Fisher according to manufacturer's protocol. Humanized EpCAM-CAR-T (PMC376) secreted high level of IFN-gamma against tested target cancer cells (FIG. 8). Humanized EpCAM-CAR-T (PMC710) also secreted high level of IFN-gamma against Lovo target cancer cells (data not shown).

Example 12

Figure 9A:
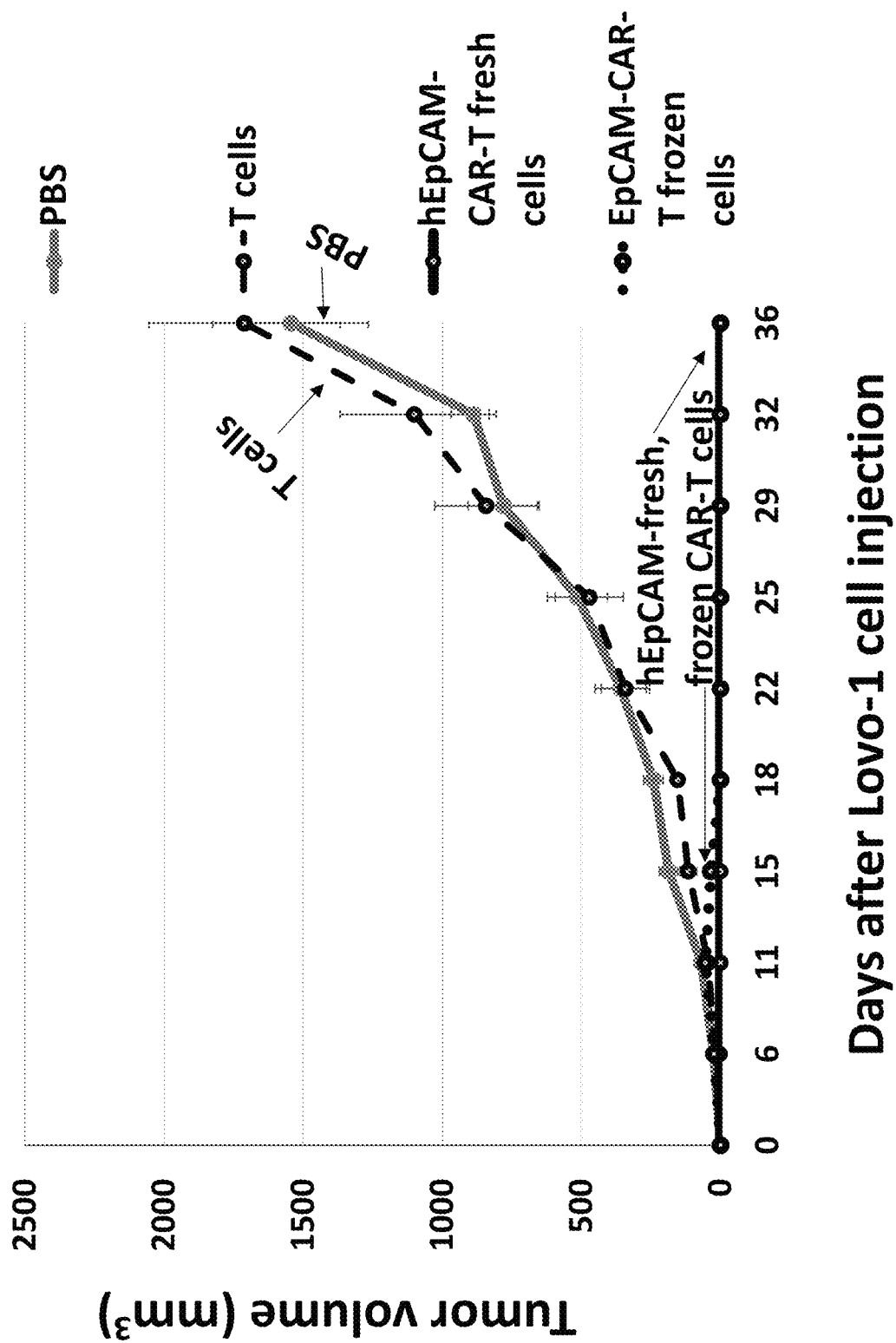
FIGS. 9A-9B show that humanized EpCAM-CAR-T cells (PMC376) significantly decreased Lovo-1 tumor volume (9A) and tumor weight (9B). p<0.05: EpCAM-CAR-T cells (fresh and frozen) versus PBS and T cells in both FIGS. 9A and 9B.
Figure 9B:
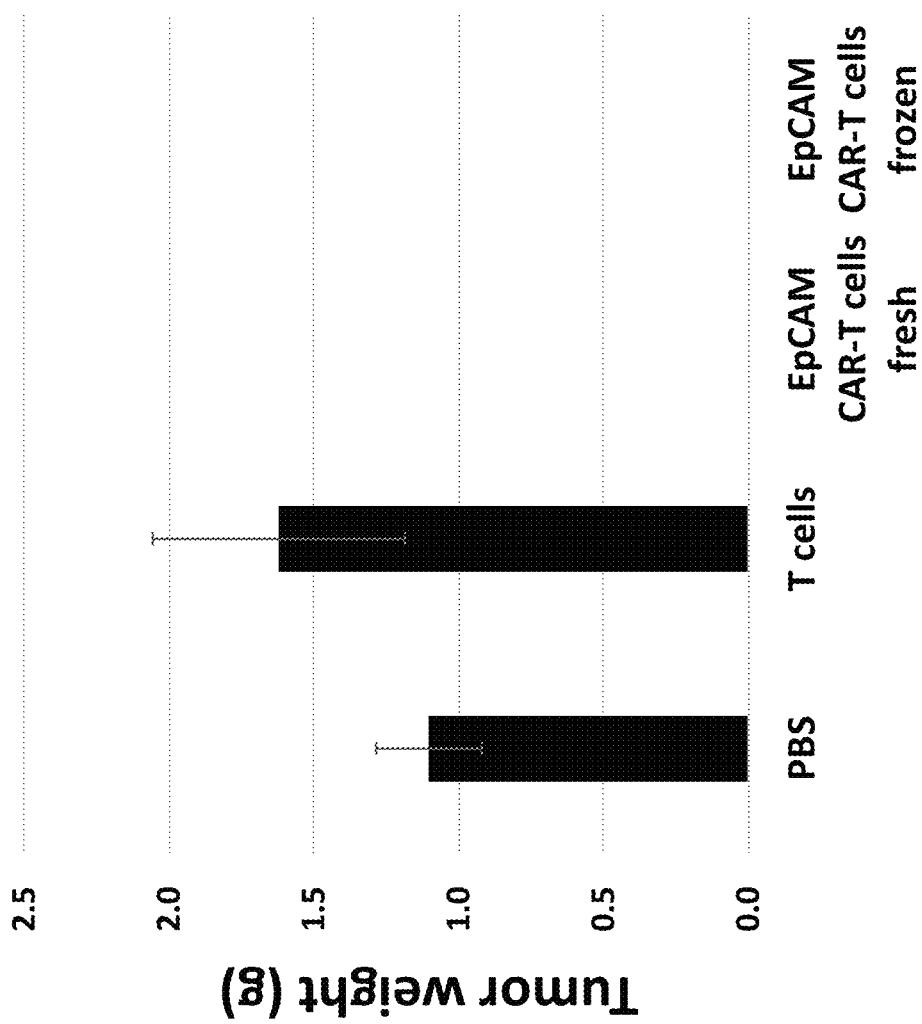

EpCAM-CAR-T Cells Significantly Decreased LOVO-1 Colon Cancer Xenograft Tumor Growth We injected Lovo-1 (colon) cancer cells subcutaneously, and next day we injected humanized EpCAM-CAR-T cells fresh or frozen intravenously. A second injection of CAR-T cells was made intravenously in a week after. Humanized EpCAM CAR-T cells completely blocked Lovo-1 tumor growth; no tumors were detected at the end of experiment (FIGS. 9A and 9B).

Figure 10:
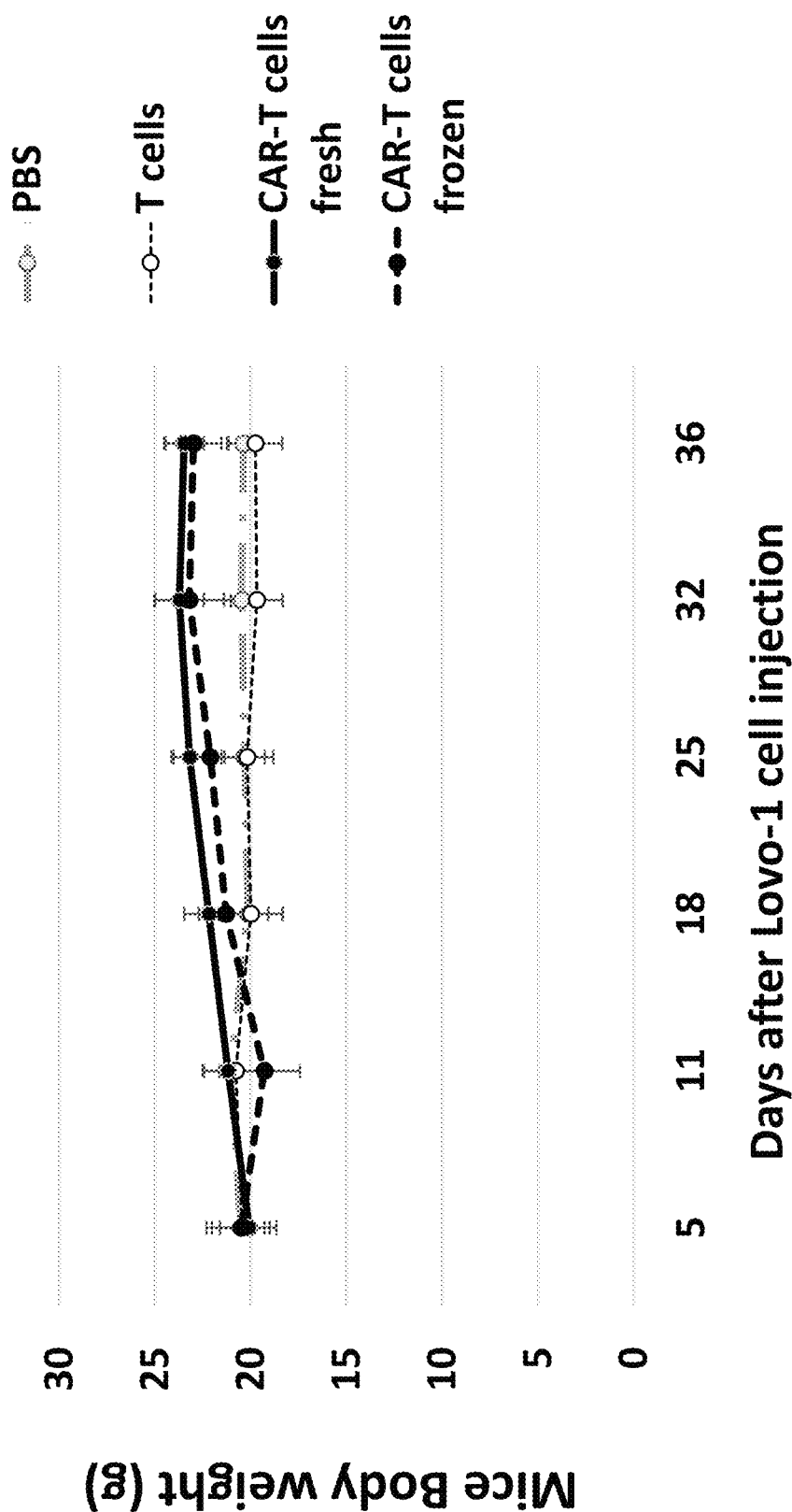
FIG. 10 shows mice treated by humanized EpCAM-CAR-T cells did not decrease body weight.

Mice from Ep-CAM-CAR-T cell-treated group did not decrease weight (FIG. 10). Thus, humanized CAR-T cells are safe and can be used as a therapeutic agent against solid tumors.

REFERENCES

1. Maus, M. V., Haas, A. R., Beatty, G. L., Albelda, S. M., Levine, B. L., Liu, X., Zhao, Y., Kalos, M., and June, C. H. (2013). T cells expressing chimeric antigen receptors can cause anaphylaxis in humans. Cancer Immunol Res 1, 26-31.
2. Maus, M. V., Grupp, S. A., Porter, D. L., and June, C. H. (2014). Antibody-modified T cells: CARs take the front seat for hematologic malignancies. Blood 123, 2625-2635.
3. Golubovskaya, Wu. Different Subsets of T Cells, Memory, Effector Functions, and CAR-T Immunotherapy. Cancers (Basel). 2016; 8(3). pii: E36. doi: 10.3390/cancers8030036
4. Epenetos, A., et al, (1982). Lancet, 2: 1004-1006
5. Durbin, G et al., Further Characterization, Isolation and Identification of the Epithelial Cell-Surface Antigen Defined by Monoclonal Antibody AUA1. Int. J. Cancer: 45, 562-565 (1990)
6. Berahovich R, Xu S, Zhou H, Harto H, Xu Q, Garcia A, Liu F, Golubovskaya V M, Wu L. FLAG-tagged CD19-specific CAR-T cells eliminate CD19-bearing solid tumor cells in vitro and in vivo. Front Biosci (Landmark Ed). 2017 Jun. 1; 22: 1644-1654

What is claimed is:

1. A humanized anti-human EpCAM antibody comprising $V_H$ having the amino acid of SEQ ID NO: 2 and $V_L$ having the amino acid of SEQ ID NO: 4.

2. A single-chain variable fragment (scFv) of a humanized anti-human EpCAM antibody comprising VH having the amino acid of SEQ ID NO: 2 and VL having the amino acid of SEQ ID NO: 4.

3. The scFv of claim 2, further comprises a linker in between $V_H$ and $V_L$.

4. The scFv of claim 2, which has the amino acid sequence of SEQ ID NO: 5.

5. A chimeric antigen receptor fusion protein (CAR) comprising from N-terminus to C-terminus;

(i) The scFv of claim 2,
(ii) a transmembrane domain,
(iii) at least one co-stimulatory domains, and
(iv) an activating domain.

6. The CAR according to claim 5, wherein the co-stimulatory domain is CD28 or 4-1BB.

7. The CAR according to claim 5, wherein the activation domain is CD3 zeta.

8. The CAR of claim 5, which has the amino acid sequence of SEQ ID NO: 16 or 19.

9. A nucleic acid encoding the CAR of claim 5.

10. T cells or natural killer cells modified to express the CAR of claim 5.

* * * * *

SEQUENCE LISTING

<160> NUMBER OF SEQ ID NOS: 19

<210> SEQ ID NO 1
<211> LENGTH: 711
<212> TYPE: DNA
<213> ORGANISM: Homo sapiens

<400> SEQUENCE: 1
caggtgcagc tggtgcagag cggcagcgaa ctgaaaaaac cgggcgcgag cgtgaaagtg      60
agctgcaaag cgagcggcta cctttacc aactatggca tgaactgggt gcgccaggcg      120
ccgggccagg gcctggaatg gatgggctgg attaacacct ataccggcga accgacctat    180
gcggatgatt ttaaaggccg ctttgtgttt agcctggata ccagcgtgag caccgcgtat    240
ctgcagatta gcagcctgaa agcggaagat accgcggtgt attattgcgc gcgctggctg    300
cgcgattttg attattgggg cgcgggcacc accgtgaccg tgagcagcgg tggcggaggt    360
tctggaggcg gtggttcagg tggcggtggt tccgaaattg tgctgaccca gagcccggcg    420 acctgagcc tgagcccggg cgaacgcgcg accctgagct gcagcgcgag cagcagcatt     480
agctatatgc attggtatca gcagaaaccg gccaggcgc cgcgcctgct gatttatgat    540
accagcaaac tggcgaccgg cattccggcg cgctttagcg gcagcggcag cggcaccgat    600
tttaccctga ccattagcag cctggaaccg gaagattttg cggtgtatta ttgccatcag    660
cgcagcagct atccgtatac ctttggcggc ggcaccaaac tggaaattaa a              711

<210> SEQ ID NO 2
<211> LENGTH: 116
<212> TYPE: PRT
<213> ORGANISM: Homo sapiens

<400> SEQUENCE: 2

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Leu Arg Asp Phe Asp Tyr Trp Gly Ala Gly Thr Thr Val
            100                 105                 110

Thr Val Ser Ser
        115

<210> SEQ ID NO 3
<211> LENGTH: 15
<212> TYPE: PRT
<213> ORGANISM: Artificial Sequence
<220> FEATURE:
<223> OTHER INFORMATION: synthetic

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 106
<212> TYPE: PRT
<213> ORGANISM: Homo sapiens

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Arg Ser Ser Tyr Pro Tyr Thr
                85                  90                  95

Phe Gly Gly Gly Thr Lys Leu Glu Ile Lys
            100                 105

<210> SEQ ID NO 5
<211> LENGTH: 237
<212> TYPE: PRT
<213> ORGANISM: Homo sapiens

<400> SEQUENCE: 5

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Leu Arg Asp Phe Asp Tyr Trp Gly Ala Gly Thr Thr Val
            100                 105                 110

Thr Val Ser Ser Gly Gly Gly Gly Ser Gly Gly Gly Gly Ser Gly Gly
            115                 120                 125

Gly Gly Ser Glu Ile Val Leu Thr Gln Ser Pro Ala Thr Leu Ser Leu
        130                 135                 140

Ser Pro Gly Glu Arg Ala Thr Leu Ser Cys Ser Ala Ser Ser Ser Ile
145                 150                 155                 160

Ser Tyr Met His Trp Tyr Gln Gln Lys Pro Gly Gln Ala Pro Arg Leu
                165                 170                 175

Leu Ile Tyr Asp Thr Ser Lys Leu Ala Thr Gly Ile Pro Ala Arg Phe
            180                 185                 190

Ser Gly Ser Gly Ser Gly Thr Asp Phe Thr Leu Thr Ile Ser Ser Leu
        195                 200                 205

Glu Pro Glu Asp Phe Ala Val Tyr Tyr Cys His Gln Arg Ser Ser Tyr
    210                 215                 220

Pro Tyr Thr Phe Gly Gly Gly Thr Lys Leu Glu Ile Lys
225                 230                 235

<210> SEQ ID NO 6
<211> LENGTH: 63
<212> TYPE: DNA
<213> ORGANISM: Homo sapiens

<400> SEQUENCE: 6
atggccttac cagtgaccgc cttgctcctg ccgctggcct tgctgctcca cgccgccagg    60
ccg                                                                  63

<210> SEQ ID NO 7
<211> LENGTH: 21
<212> TYPE: PRT
<213> ORGANISM: Homo sapiens

<400> SEQUENCE: 7

Met Ala Leu Pro Val Thr Ala Leu Leu Leu Pro Leu Ala Leu Leu Leu
1               5                   10                  15

His Ala Ala Arg Pro
            20

<210> SEQ ID NO 8
<211> LENGTH: 135
<212> TYPE: DNA
<213> ORGANISM: Homo sapiens

<400> SEQUENCE: 8
accacgacgc cagcgccgcg accaccaaca ccggcgccca ccatcgcgtc gcagcccctg    60
tccctgcgcc agaggcgag ccggccagcg gcggggggcg cagtgcacac gaggggctg    120 gacttcgcca gtgat                                                   135

<210> SEQ ID NO 9
<211> LENGTH: 45
<212> TYPE: PRT
<213> ORGANISM: Homo sapiens

<400> SEQUENCE: 9

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Ser Arg Pro Ala Ala Gly
            20                  25                  30

Gly Ala Val His Thr Arg Gly Leu Asp Phe Ala Ser Asp
            35                  40                  45

<210> SEQ ID NO 10
<211> LENGTH: 81
<212> TYPE: DNA
<213> ORGANISM: Homo sapiens

<400> SEQUENCE: 10
ttttgggtgc tggtggtggt tggtggagtc ctggcttgct atagcttgct agtaacagtg    60
gcctttatta ttttctgggt g                                              81

<210> SEQ ID NO 11
<211> LENGTH: 27
<212> TYPE: PRT
<213> ORGANISM: Homo sapiens

<400> SEQUENCE: 11

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 12
<211> LENGTH: 123
<212> TYPE: DNA
<213> ORGANISM: Homo sapiens

<400> SEQUENCE: 12

```
aggagtaaga ggagcaggct cctgcacagt gactacatga acatgactcc ccgccgcccc   60
gggcccaccc gcaagcatta ccagccctat gccccaccac gcgacttcgc agcctatcgc  120
tcc                                                                123
```

<210> SEQ ID NO 13
<211> LENGTH: 41
<212> TYPE: PRT
<213> ORGANISM: Homo sapiens

<400> SEQUENCE: 13

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40
```

<210> SEQ ID NO 14
<211> LENGTH: 342
<212> TYPE: DNA
<213> ORGANISM: Homo sapiens

<400> SEQUENCE: 14

```
agagtgaagt tcagcaggag cgcagacgcc cccgcgtacc agcagggcca gaaccagctc   60
tataacgagc tcaatctagg acgaagagag gagtacgatg ttttggacaa gagacgtggc  120
cgggaccctg agatgggggg aaagccgcag agaaggaaga accctcagga aggcctgtac  180
aatgaactgc agaaagataa gatggcggag gcctacagtg agattgggat gaaaggcgag  240
cgccggaggg gcaaggggca cgatggcctt taccagggtc tcagtacagc caccaaggac  300
acctacgacg cccttcacat gcaggccctg ccccctcgct aa                     342
```

<210> SEQ ID NO 15
<211> LENGTH: 113
<212> TYPE: PRT
<213> ORGANISM: Homo sapiens

<400> SEQUENCE: 15

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
            50                  55                  60

Lys Asp Lys Met Ala Glu Ala Tyr Ser Glu Ile Gly Met Lys Gly Glu
```

```
              65                  70                  75                  80
Arg Arg Arg Gly Lys Gly His Asp Gly Leu Tyr Gln Gly Leu Ser Thr
                    85                  90                  95
Ala Thr Lys Asp Thr Tyr Asp Ala Leu His Met Gln Ala Leu Pro Pro
                    100                 105                 110
Arg

<210> SEQ ID NO 16
<211> LENGTH: 492
<212> TYPE: PRT
<213> ORGANISM: Homo sapiens

<400> SEQUENCE: 16

Met Ala Leu Pro Val Thr Ala Leu Leu Leu Pro Leu Ala Leu Leu Leu
1               5                   10                  15

His Ala Ala Arg Pro Ala Ser Gln Val Gln Leu Val Gln Ser Gly Ser
                20                  25                  30

Glu Leu Lys Lys Pro Gly Ala Ser Val Lys Val Ser Cys Lys Ala Ser
            35                  40                  45

Gly Tyr Thr Phe Thr Asn Tyr Gly Met Asn Trp Val Arg Gln Ala Pro
        50                  55                  60

Gly Gln Gly Leu Glu Trp Met Gly Trp Ile Asn Thr Tyr Thr Gly Glu
65                  70                  75                  80

Pro Thr Tyr Ala Asp Asp Phe Lys Gly Arg Phe Val Phe Ser Leu Asp
                85                  90                  95

Thr Ser Val Ser Thr Ala Tyr Leu Gln Ile Ser Ser Leu Lys Ala Glu
                100                 105                 110

Asp Thr Ala Val Tyr Tyr Cys Ala Arg Trp Leu Arg Asp Phe Asp Tyr
            115                 120                 125

Trp Gly Ala Gly Thr Thr Val Thr Val Ser Ser Gly Gly Gly Gly Ser
        130                 135                 140

Gly Gly Gly Gly Ser Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Ser Ala Ser Ser Ser Ile Ser Tyr Met His Trp Tyr Gln Gln Lys
            180                 185                 190

Pro Gly Gln Ala Pro Arg Leu Leu Ile Tyr Asp Thr Ser Lys Leu Ala
        195                 200                 205

Thr Gly Ile Pro Ala Arg Phe Ser Gly Ser Gly Ser Gly Thr Asp Phe
    210                 215                 220

Thr Leu Thr Ile Ser Ser Leu Glu Pro Glu Asp Phe Ala Val Tyr Tyr
225                 230                 235                 240

Cys His Gln Arg Ser Ser Tyr Pro Tyr Thr Phe Gly Gly Gly Thr Lys
                245                 250                 255

Leu Glu Ile Lys Leu Glu Lys Pro Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Ser Arg Pro Ala Ala Gly Gly Ala Val His Thr Arg Gly Leu
    290                 295                 300

Asp Phe Ala Ser Asp Lys Pro Phe Trp Val Leu Val Val Val Gly Gly
305                 310                 315                 320

Val Leu Ala Cys Tyr Ser Leu Leu Val Thr Val Ala Phe Ile Ile Phe
```

-continued

```
                325                 330                 335
Trp Val Arg Ser Lys Arg Ser Arg Leu Leu His Ser Asp Tyr Met Asn
            340                 345                 350
Met Thr Pro Arg Arg Pro Gly Pro Thr Arg Lys His Tyr Gln Pro Tyr
            355                 360                 365
Ala Pro Pro Arg Asp Phe Ala Ala Tyr Arg Ser Arg Val Lys Phe Ser
        370                 375                 380
Arg Ser Ala Asp Ala Pro Ala Tyr Gln Gln Gly Gln Asn Gln Leu Tyr
385                 390                 395                 400
Asn Glu Leu Asn Leu Gly Arg Arg Glu Tyr Asp Val Leu Asp Lys
                405                 410                 415
Arg Arg Gly Arg Asp Pro Glu Met Gly Gly Lys Pro Gln Arg Arg Lys
            420                 425                 430
Asn Pro Gln Glu Gly Leu Tyr Asn Glu Leu Gln Lys Asp Lys Met Ala
            435                 440                 445
Glu Ala Tyr Ser Glu Ile Gly Met Lys Gly Glu Arg Arg Arg Gly Lys
        450                 455                 460
Gly His Asp Gly Leu Tyr Gln Gly Leu Ser Thr Ala Thr Lys Asp Thr
465                 470                 475                 480
Tyr Asp Ala Leu His Met Gln Ala Leu Pro Pro Arg
                485                 490
```

<210> SEQ ID NO 17
<211> LENGTH: 126
<212> TYPE: DNA
<213> ORGANISM: Homo sapiens

<400> SEQUENCE: 17

```
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126
```

<210> SEQ ID NO 18
<211> LENGTH: 42
<212> TYPE: PRT
<213> ORGANISM: Homo sapiens

<400> SEQUENCE: 18

```
Lys Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
            20                  25                  30
Pro Glu Glu Glu Glu Gly Gly Cys Glu Leu
        35                  40
```

<210> SEQ ID NO 19
<211> LENGTH: 493
<212> TYPE: PRT
<213> ORGANISM: Homo sapiens

<400> SEQUENCE: 19

```
Met Ala Leu Pro Val Thr Ala Leu Leu Leu Pro Leu Ala Leu Leu Leu
1               5                   10                  15
His Ala Ala Arg Pro Ala Ser Gln Val Gln Leu Val Gln Ser Gly Ser
            20                  25                  30
Glu Leu Lys Lys Pro Gly Ala Ser Val Lys Val Ser Cys Lys Ala Ser
        35                  40                  45
```

-continued

Gly Tyr Thr Phe Thr Asn Tyr Gly Met Asn Trp Val Arg Gln Ala Pro
            50                  55                  60

Gly Gln Gly Leu Glu Trp Met Gly Trp Ile Asn Thr Tyr Thr Gly Glu
65                  70                  75                  80

Pro Thr Tyr Ala Asp Asp Phe Lys Gly Arg Phe Val Phe Ser Leu Asp
                85                  90                  95

Thr Ser Val Ser Thr Ala Tyr Leu Gln Ile Ser Ser Leu Lys Ala Glu
            100                 105                 110

Asp Thr Ala Val Tyr Tyr Cys Ala Arg Trp Leu Arg Asp Phe Asp Tyr
            115                 120                 125

Trp Gly Ala Gly Thr Thr Val Thr Val Ser Ser Gly Gly Gly Gly Ser
            130                 135                 140

Gly Gly Gly Gly Ser Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Ser Ala Ser Ser Ile Ser Tyr Met His Trp Tyr Gln Gln Lys
            180                 185                 190

Pro Gly Gln Ala Pro Arg Leu Leu Ile Tyr Asp Thr Ser Lys Leu Ala
            195                 200                 205

Thr Gly Ile Pro Ala Arg Phe Ser Gly Ser Gly Ser Gly Thr Asp Phe
210                 215                 220

Thr Leu Thr Ile Ser Ser Leu Glu Pro Glu Asp Phe Ala Val Tyr Tyr
225                 230                 235                 240

Cys His Gln Arg Ser Ser Tyr Pro Tyr Thr Phe Gly Gly Gly Thr Lys
                245                 250                 255

Leu Glu Ile Lys Leu Glu Lys Pro Thr Thr Thr Pro Ala Pro Arg Pro
            260                 265                 270

Pro Thr Pro Ala Pro Thr Ile Ala Ser Gln Pro Leu Ser Leu Arg Pro
            275                 280                 285

Glu Ala Ser Arg Pro Ala Ala Gly Gly Ala Val His Thr Arg Gly Leu
            290                 295                 300

Asp Phe Ala Ser Asp Lys Pro Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
            355                 360                 365

Arg Phe Pro Glu Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Gln Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

-continued

```
Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```